(12) United States Patent
Sanai et al.

(10) Patent No.: US 9,801,675 B2
(45) Date of Patent: Oct. 31, 2017

(54) TREATMENT ASSEMBLY, TREATMENT DEVICE AND MANUFACTURING METHOD OF TREATMENT DEVICE

(71) Applicant: OLYMPUS CORPORATION, Tokyo (JP)

(72) Inventors: Hideo Sanai, Hachioji (JP); Kenichi Kimura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 44 days.

(21) Appl. No.: 14/278,644

(22) Filed: May 15, 2014

(65) Prior Publication Data
US 2014/0324084 A1   Oct. 30, 2014

Related U.S. Application Data

(63) Continuation of application No. PCT/JP2013/069188, filed on Jul. 12, 2013.
(Continued)

(51) Int. Cl.
*A61B 17/32* (2006.01)
*A61B 18/00* (2006.01)
(Continued)

(52) U.S. Cl.
CPC ...... *A61B 18/00* (2013.01); *A61B 17/320068* (2013.01); *A61B 18/1482* (2013.01);
(Continued)

(58) Field of Classification Search
CPC .......... A61B 17/320068; A61B 2017/320072; A61B 2017/320076; A61B 2017/320088;
(Continued)

(56) References Cited

U.S. PATENT DOCUMENTS

| 4,431,006 A | 2/1984 | Trimmer et al. |
| 5,346,502 A | 9/1994 | Estabrook et al. |

(Continued)

FOREIGN PATENT DOCUMENTS

| JP | A-8-509628 | 10/1996 |
| JP | A-11-318918 | 11/1999 |

OTHER PUBLICATIONS

International Search Report issued in International Patent Application No. PCT/JP2013/069188 dated Aug. 27, 2013.
(Continued)

*Primary Examiner* — Tuan V Nguyen
*Assistant Examiner* — Christian Knauss
(74) *Attorney, Agent, or Firm* — Oliff PLC

(57) ABSTRACT

A treatment assembly includes: a probe which includes a treatment section at a distal end portion thereof; an inner tube which includes a distal end and into which the probe is inserted in a state that the treatment section of the probe protrudes toward a distal end side with respect to the distal end; an opening which is provided in a side surface of the inner tube and which allows an inner side of the inner tube to communicate with an outer side of the inner tube; a support section which is arranged on the inner side of the inner tube from the outer side of the inner tube through the opening and which is configured to support the probe with respect to the inner tube; and an outer tube which covers the outer side of the inner tube and which is configured to fix the support section.

17 Claims, 20 Drawing Sheets

Related U.S. Application Data

(60) Provisional application No. 61/704,772, filed on Sep. 24, 2012.

(51) Int. Cl.
*A61N 7/00* (2006.01)
*A61B 18/14* (2006.01)
*A61B 17/00* (2006.01)

(52) U.S. Cl.
CPC ...... *A61N 7/00* (2013.01); *A61B 2017/00477* (2013.01); *A61B 2017/00526* (2013.01); *A61B 2017/320072* (2013.01); *A61B 2017/320088* (2013.01); *A61B 2018/0091* (2013.01); *A61B 2018/1422* (2013.01); *A61B 2018/1475* (2013.01); *Y10T 29/49826* (2015.01)

(58) Field of Classification Search
CPC .. A61B 2018/1422; A61B 2017/00477; A61B 2017/00526; A61N 2007/0008; A61C 3/03; A61F 9/00745
See application file for complete search history.

(56) References Cited

U.S. PATENT DOCUMENTS

| | | | |
|---|---|---|---|
| 5,449,370 A | | 9/1995 | Vaitekunas |
| 5,897,523 A | * | 4/1999 | Wright et al. .................. 604/22 |
| 5,935,144 A | * | 8/1999 | Estabrook ...... A61B 17/320068 604/22 |
| 6,206,844 B1 | * | 3/2001 | Reichel .......... A61B 17/320068 600/121 |
| 6,613,056 B1 | | 9/2003 | Brumbach et al. |
| 2001/0027325 A1 | * | 10/2001 | Beaupre ......... A61B 17/320068 606/169 |
| 2008/0234710 A1 | * | 9/2008 | Neurohr ......... A61B 17/320068 606/169 |

OTHER PUBLICATIONS

Dated Apr. 2, 2015 International Preliminary Report on Patentability issued in International Application No. PCT/JP2013/069188.
Dated Apr. 29, 2016 Extended European Search Report issued in European Patent Application No. 13838563.8.
Dated Mar. 8, 2017 Office Action issued in Chinese Patent Application No. 201380049771.3.

* cited by examiner

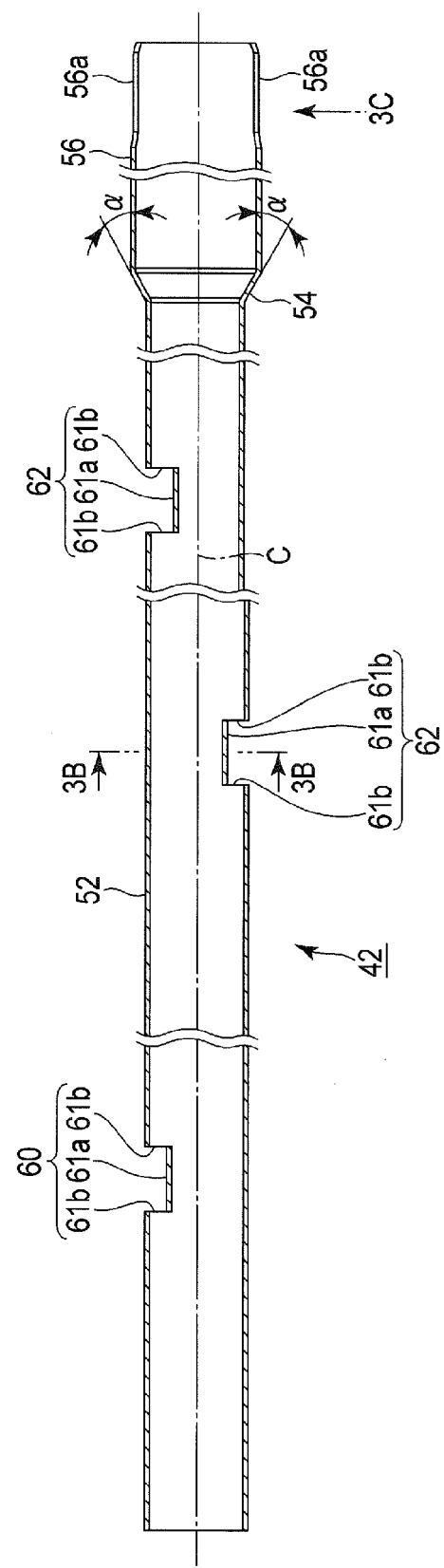
F I G. 3A

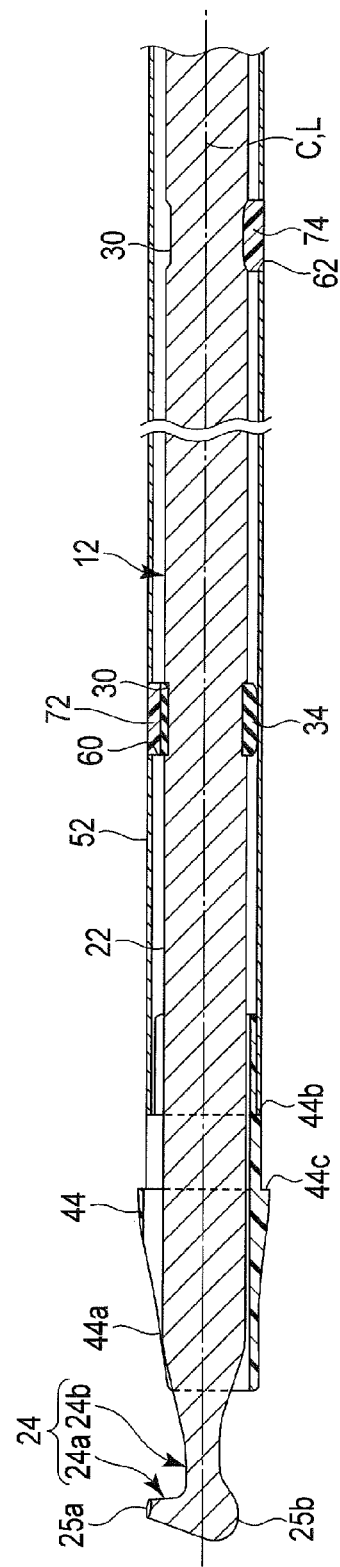
F I G. 6A

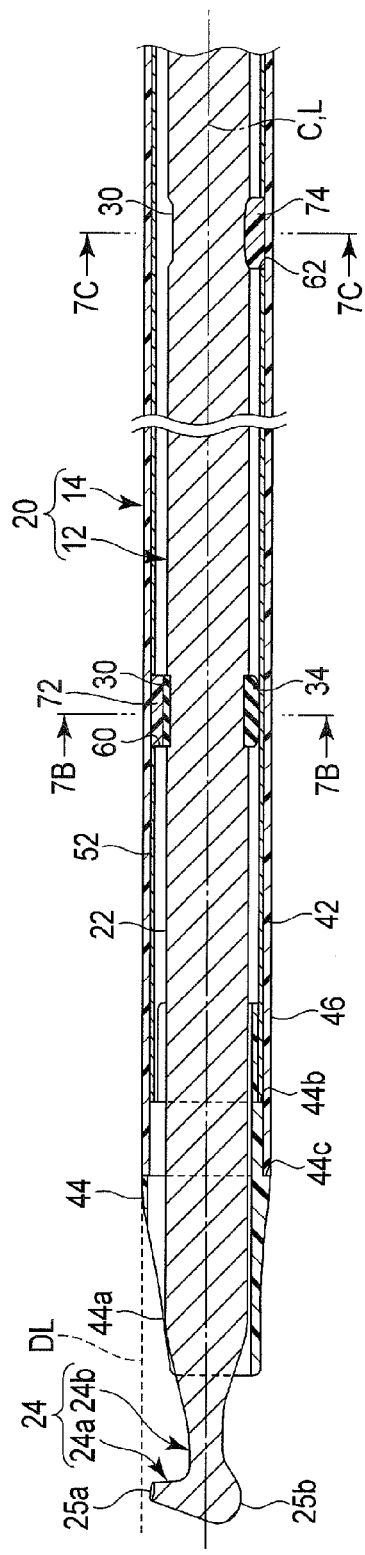
F I G. 7A

TREATMENT ASSEMBLY, TREATMENT DEVICE AND MANUFACTURING METHOD OF TREATMENT DEVICE

CROSS-REFERENCE TO RELATED APPLICATIONS

This application is a Continuation Application of PCT Application No. PCT/JP2013/069188, filed Jul. 12, 2013 and based upon and claiming the benefit of priority from U.S. Provisional Application No. 61/704,772, filed Sep. 24, 2012, the entire contents of all of which are incorporated herein by reference.

BACKGROUND OF THE INVENTION

1. Field of the Invention

The present invention relates to a treatment assembly and a treatment device which is configured to treat a biological tissue, and a manufacturing method of the treatment assembly.

2. Description of the Related Art

For example, like a treatment device described in U.S. Pat. No. 5,449,370A, on an outer peripheral surface of a probe of an ultrasonic treatment device, an O-ring (a heat-resisting electrical insulation material) having an outer peripheral surface provided on a radially outer side relative to a probe main body portion is generally arranged at a node position of vibration. The outer peripheral surface of each O-ring is arranged to contact on an inner peripheral surface of a sheath so that a central axis of the sheath coincides with a longitudinal axis of the probe, and a distance is assured between an outer peripheral surface of the probe main body portion and the inner peripheral surface of the sheath. Further, each O-ring achieves air-tightness and water-tightness between the outer peripheral surface of the probe and the inner peripheral surface of the sheath.

For example, a circular acoustic isolation element is fixed on an outer peripheral surface of a probe of a treatment device disclosed in U.S. Pat. No. 5,935,144A by, e.g., injection molding. The probe is coupled with a sheath by matching a central axis of the sheath with a longitudinal axis of the probe and injecting a sealing material into a region between the acoustic isolation element and an inner peripheral surface of the sheath.

BRIEF SUMMARY OF THE INVENTION

According to one embodiment of the present invention, a treatment assembly includes: a probe which includes a treatment section at a distal end portion thereof; an inner tube which includes a distal end and into which the probe is inserted in a state that the treatment section of the probe protrudes toward a distal end side with respect to the distal end; an opening which is provided in a side surface of the inner tube and which allows an inner side of the inner tube to communicate with an outer side of the inner tube; a support section which is arranged on the inner side of the inner tube from the outer side of the inner tube through the opening and which is configured to support the probe with respect to the inner tube; and an outer tube which covers the outer side of the inner tube and which is configured to fix the support section.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3A is a schematic longitudinal cross-sectional view showing an inner tube of a sheath of the treatment device according to the first embodiment;

FIG. 6A is a schematic longitudinal cross-sectional view showing a status that an arc-shaped body and a support member are arranged through an opening in a side surface of the inner tube in a state that the probe is inserted from the proximal end side toward the distal end side of the inner tube of the sheath of the treatment device according to the first embodiment and the distal end pipe is likewise inserted;

FIG. 7A is a schematic longitudinal cross-sectional view showing a treatment assembly in which an outer tube is arranged on the outer side of the inner tube and the outer side of the distal end pipe in a state that the probe is inserted from the proximal end side toward the distal end side of the inner tube of the sheath of the treatment device according to the first embodiment, the distal end pipe is arranged at the distal end of the inner tube, and the arc-shaped body and the support member are arranged through the opening in the side surface of the inner tube;

DETAILED DESCRIPTION OF THE INVENTION

Modes for embodying the present invention will now be described with reference to the drawings.

A description will be given as to a first embodiment with reference to FIG. 1A to FIG. 8.

Figure 1A:
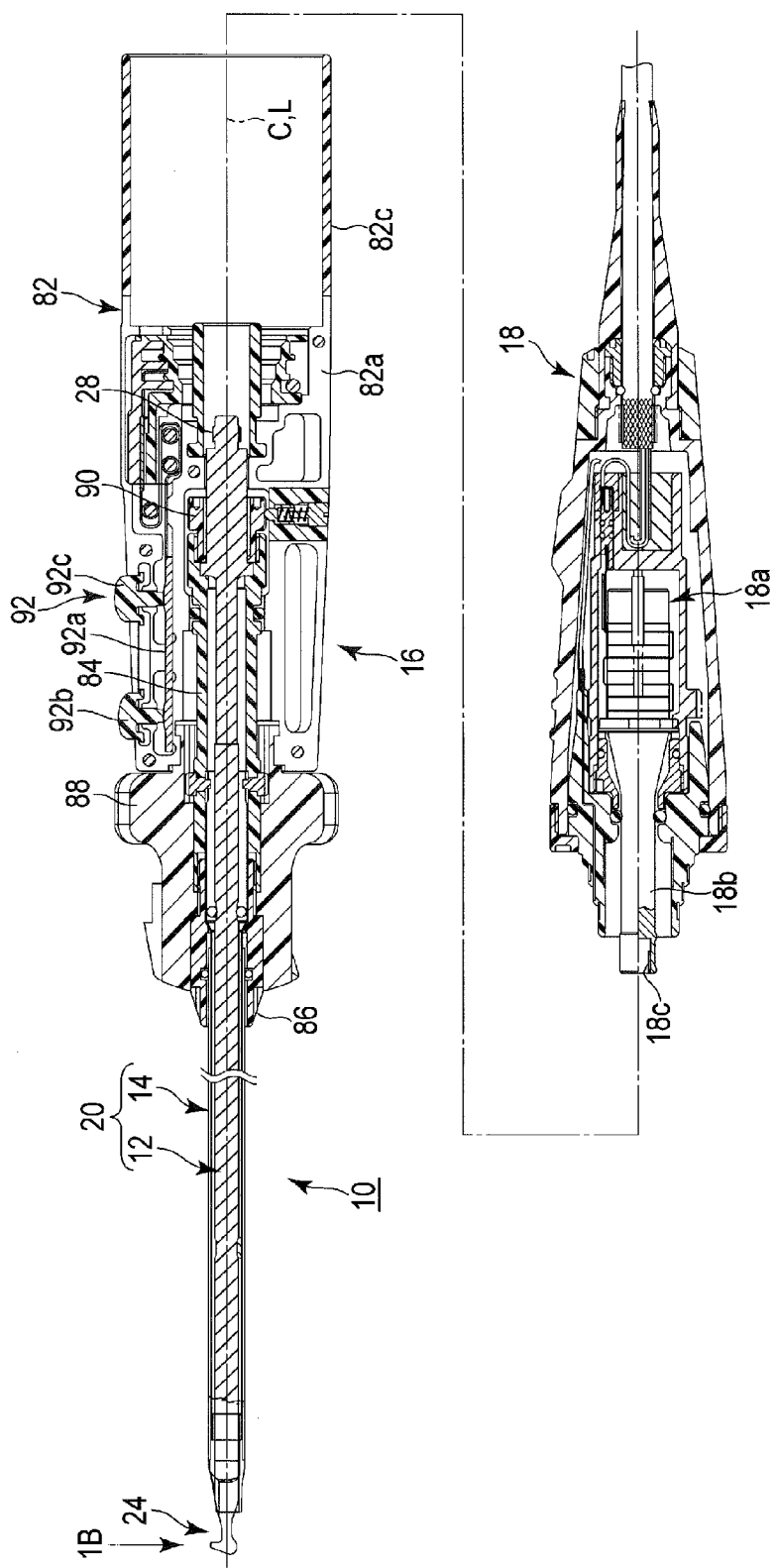
FIG. 1A is a schematic longitudinal cross-sectional view showing a treatment device according to first and second embodiments of the present invention and also showing a state seen from a direction of an arrow 1A in FIG. 1B.
Figure 1B:
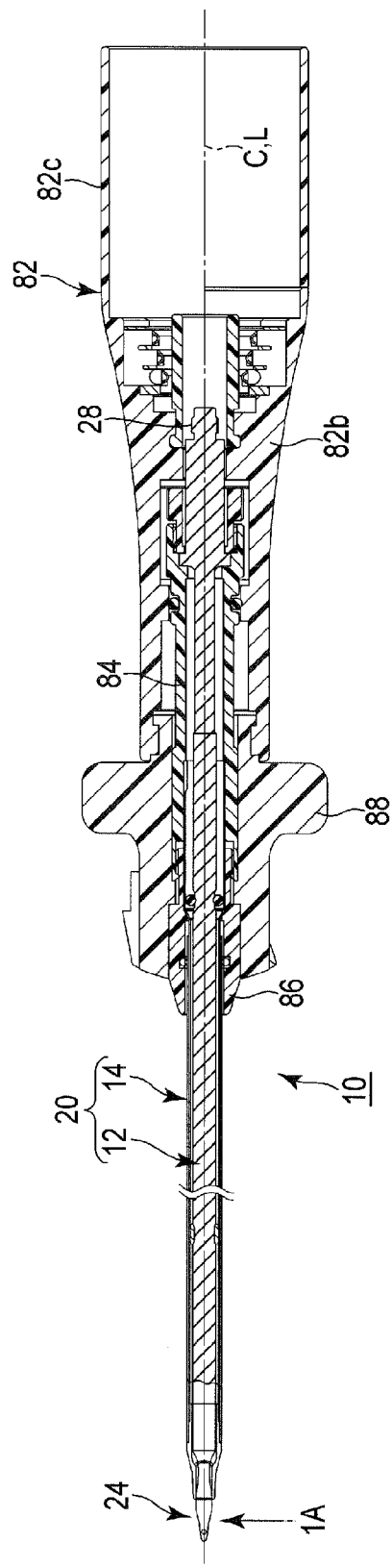
FIG. 1B is a schematic longitudinal cross-sectional view showing the treatment device according to the first and second embodiments and also showing a state seen from a direction of an arrow 1B in FIG. 1A.

As shown in FIG. 1A and FIG. 1B, a treatment device 10 according to this embodiment has a probe 12, an elongated sheath 14 into which the probe 12 is inserted, and a handle (an operating section) 16 arranged at a proximal end of the sheath 14. A central axis C is defined by a distal end and a proximal end of the sheath 14.

An ultrasonic transducer unit 18 having an ultrasonic transducer 18a that is connected to an ultrasonic vibration energy source (not shown) and gives the probe 12 ultrasonic vibration energy can be attached to or detached from the treatment device 10 according to this embodiment. In addition, it is preferable for the treatment device 10 according to this embodiment to be connected to a high-frequency energy source (not shown) that gives the probe 12 high-frequency energy in addition to the connection to the ultrasonic vibration energy source through the ultrasonic transducer unit 18.

Figure 2A:
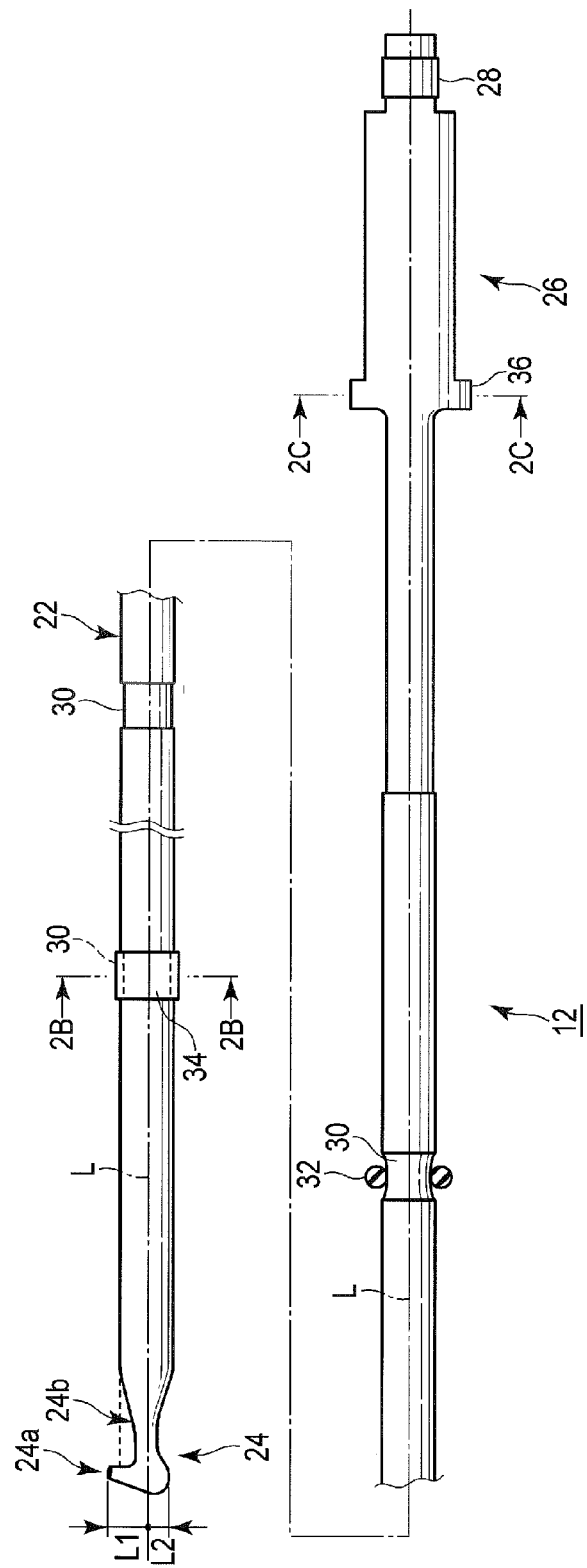
FIG. 2A is a schematic side view showing a probe of the treatment device according to the first embodiment.

The probe 12 shown in FIG. 2A is made of, e.g., a titanium alloy or the like. The probe 12 is a probe main body section 22, a treatment section 22 (a probe distal end portion) 24 that is provided on a distal end direction side of the probe main body section 22 and is able to treat a biological tissue, and a horn (a probe proximal end portion) 26 that is provided on a proximal end direction side of the probe main body section 22 and increases an amplitude of ultrasonic vibration. In the following description, it is assumed that a longitudinal axis L of the probe 12 is provided on a central axis defined by a distal end portion and a proximal end portion of the probe main body section 22.

It is to be noted that a coupling section (a screw section) 28 is formed at a proximal end of the probe 12. In this embodiment, a description will be given on the assumption that the coupling section 28 is a screw section. The coupling section 28 at the proximal end of the probe 12 can be attached to or detached from a coupling section (a screw section) 18c at a distal end of a fixing member 18b fixed to the ultrasonic transducer 18a shown in FIG. 1A. The fixing member 18b is made of the same material as the probe 12 that is made of, e.g., a titanium alloy.

A length of the probe 12 is determined based on a resonance frequency of the ultrasonic transducer 18a connected to the treatment device 10. A node position of vibration of ultrasonic vibration is determined based on the resonance frequency. In the probe main body section 22, annular grooves 30 each having an outer diameter smaller than an outer diameter of an adjacent region is formed at a position corresponding to the node position of the vibration of the ultrasonic vibration to support the probe 12 at a predetermined position with respect to the sheath 14. An O-ring 32 that is configured to achieve air-tightness or liquid-tightness between the probe main body section 22 and an inner tube 42 of the sheath 14 or suppression of inappropriate vibration of the ultrasonic vibration is arranged between an inner peripheral surface of a proximal end portion of the later-described inner tube 42 of the sheath 14 and an outer peripheral surface of the annular grooves 30. This O-ring 32 is made of, e.g., a PTFE material having electric insulation properties and heat-resisting properties. In the case of arranging the ultrasonic transducer unit 18 at the proximal end of the handle 16 and using a non-illustrated trocar for the treatment device 10 to carry out laparoscopic surgery or the like, pneumoperitoneum must be performed with the use of a gas such as carbon dioxide or the like. When the O-ring 32 is arranged between the outer peripheral surface of the annular grooves 30 and the inner peripheral surface of the sheath 14, the gas can be prevented from being removed from the abdominal cavity through a space between the probe 12 and the sheath 14.

Figure 2B:
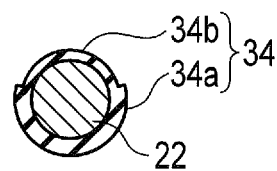
FIG. 2B is a schematic transverse cross-sectional view showing the probe of the treatment device according to the first embodiment taken along a line of arrows 2B-2B in FIG. 2A.

An annular body 34 is arranged in the annular groove 30 out of the annular grooves 30 of the probe main body section 22 that is closest to the treatment section 24 outside the handle 16. As shown in FIG. 2B, the annular body 34 includes an annular portion 34a and an arc-shaped concave portion 34b formed by removing part of the outer side of the annular portion 34a in an arc-like shape. The annular body 34 is made of an elastically deformable material such as a rubber material, and an outer peripheral surface of the largest diameter portion of the annular portion 34a relative to the longitudinal axis L is provided on the radially outer side of the outer peripheral surface of the probe main body section 22. The annular portion 34a of the annular body 34 in particular appropriately elastically deforms at the time of passing the probe 12 from the proximal end toward the distal end of the sheath 14. It is to be noted that an arc-shaped body (a support section) 72 (see FIG. 6B and FIG. 7B) made of a resin material is arranged in the arc-shaped concave portion 34b through an opening 60 of the later-described inner tube 42 of the sheath 14. The arc-shaped body 72 is formed into a size that enables press-fitting into the opening 60. The arc-shaped body 72 has an engagement section 72a that engages with a first edge portion 61a (see FIG. 3A and FIG. 3B) of the opening 60 of the inner tube 42 at each of end portions (one end and the other end). The engagement section 72a of the arc-shaped body 72 is engaged with the first edge portion 61a of the opening 60 of the inner tube 42, and the arc-shaped body 72 is closely fitted to the outer periphery of the arc-shaped concave portion 34b. In this state, when an outer tube 46 of the sheath 14 is arranged on the outer side of the inner tube 42, air-tightness and liquid-tightness can be achieved between the probe main body section 22 and the sheath 14.

As the annular grooves 30 of the probe main body section 2, there are annular grooves 30 between the annular groove 30 which is closest to the treatment section 24 and in which the annular body 34 is arranged and the annular groove 30 in which the O-ring 32 is arranged. Of these annular grooves 30, it is preferable to arrange a later-described support member 74 (see FIG. 6C and FIG. 7C) which supports the annular groove 30 through the later-described opening 62 in the inner tube 42 of the sheath 14 in the first annular groove 30 on the distal end side relative to the distal end of the handle 16.

Further, in the annular groove 30 between the annular groove 30 which is closest to the treatment section 24 and in which the annular body 34 is arranged and the first annular groove 30 on the distal end side relative to the distal end of the handle 16, it is also preferable to arrange the same support member 74 as the support member 74 arranged in the first annular groove 30 on the distal end side relative to the distal end of the handle 16.

It is to be noted that, in the case of adopting a resonance frequency 47 kHz of the ultrasonic transducer 18a of the ultrasonic transducer unit 18, an interval of node positions of vibration of the probe 12, i.e., an interval between the annular grooves 30 adjacent to each other is approximately 50 mm. Furthermore, a later-described asymmetrical portion 24a of the treatment section 24 corresponds to an anti-node position of the vibration.

The treatment section 24 is asymmetrical with respect to the longitudinal axis L of the probe main body section 22 and formed to be slightly smaller than an inner diameter of the sheath 14 as a whole. Specifically, for example, as shown in FIG. 2A, the treatment section 24 includes an asymmetrical portion 24a that is arranged to contact on a biological tissue and a coupling portion 24b that is integrally coupled between the distal end of the probe main body section 22 and the asymmetrical portion 24a. In addition, it is preferable for a transverse cross section of the coupling portion 24b to be present on the inner side of the outer peripheral surface of the probe main body section 22.

Figure 4:
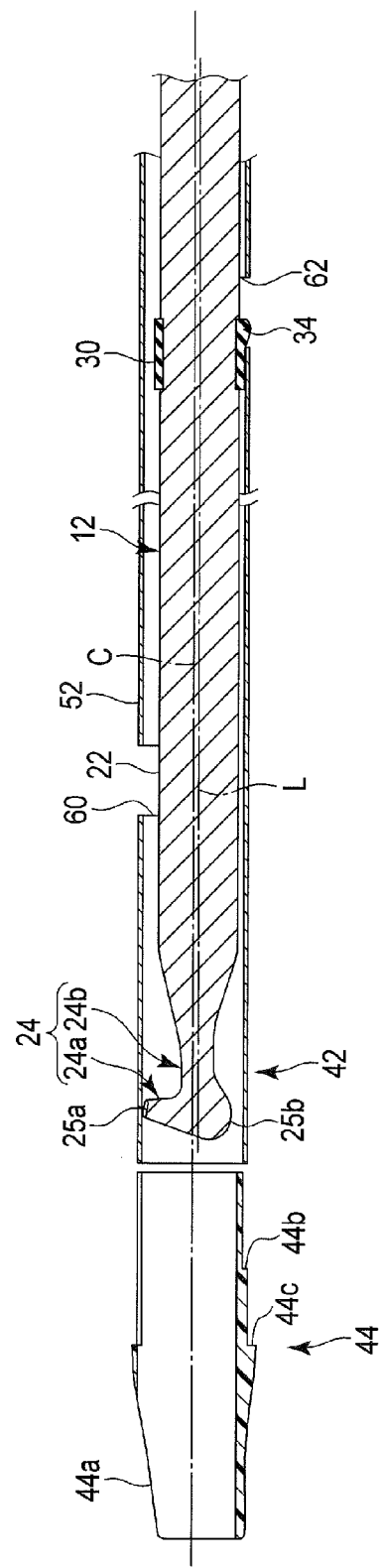
FIG. 4 is a schematic longitudinal cross-sectional view showing a state that the probe is inserted from a proximal end side toward a distal end side of the inner tube of the sheath of the treatment device according to the first embodiment and also showing a state that a distal end pipe is arranged at a distal end of the inner tube.

In the asymmetrical portion 24a of the treatment section 24, for example, as shown in FIG. 2A, a distance L1 between the longitudinal axis L and a distal tip 25a on the upper side of the longitudinal axis L is larger than a distance L2 between the longitudinal axis L and a proximal tip 25b on the lower side of the longitudinal axis L. That is, as shown in FIG. 4, the distal end portion of the probe 12 has the distal tip 25a that has a shape asymmetrical with respect to the longitudinal axis L and is away from the longitudinal axis L and the proximal tip 25b that is close to the longitudinal axis L as compared with the distal tip 25a. Here, a length obtained by adding the distances L1 and L2 is slightly smaller than the minimum inner diameter of the inner tube 42 of the sheath 14 in this embodiment. Therefore, in the case of inserting the treatment section 24 of the probe 12 from the proximal end toward the distal end, the probe 12 is inserted into the sheath 14 in a state that the longitudinal axis L of the probe 12 deviates from the central axis C of the sheath 14. When the probe 12 is arranged at a predetermined position of the sheath 14, the longitudinal axis L of the probe main body section 22 coincides with the central axis C of the sheath 14. It is to be noted that, in this specification, "the longitudinal axis L of the probe main body section 22 coincides with the central axis C of the sheath 14" includes perfect matching of these members as well as slight deviation, i.e., substantial matching of the same.

It is to be noted that the asymmetrical portion 24a of the treatment section 24 is not restricted to, e.g., a hook shape shown in FIG. 1A, FIG. 1B, and FIG. 2A, and it may be formed into a spatula-like shape or the like. In this case, likewise, in the asymmetrical portion 24a of the treatment section 24, the distance L1 between the longitudinal axis L and the distal tip on the upper side of the longitudinal axis is larger than the distance L2 between the longitudinal axis L and the distal tip on the lower side of the longitudinal axis, and a length obtained by adding the distances L1 and L2 is slightly smaller than the inner diameter of the inner tube 42 of the sheath 14.

Figure 2C:
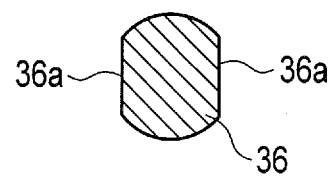
FIG. 2C is a schematic transverse cross-sectional view showing the probe of the treatment device according to the first embodiment taken along a line of arrows 2C-2C in FIG. 2A.

The horn 26 is formed to be larger than the outer diameter of the probe main body section 22. As shown in FIG. 2C, the horn 26 has, e.g., a fitting section 36 having one or more flat surfaces 36a so that locking and fitting can be performed at the node position of the vibration with respect to a later-described holder 84 of the handle 16. Moreover, the node position of the vibration in the horn 26 is pushed and supported by a later-described fixing member 90 (see FIG. 1A, FIG. 1B, and FIG. 8) from the proximal end side so that movement of the horn 26 in the axial direction relative to the holder 84 can be regulated.

As shown in FIG. 3A to FIG. 7C, the sheath 14 includes the inner tube 42 made of a metal material such as stainless steel, a distal end pipe (a distal end cover) 44 made of a resin material such as a PTFE material, and an outer tube 46 such as a heat shrinkable tube that has electric insulation properties and covers the outer side of the inner tube 42 made of the metal material. Although an outer diameter of the sheath 14 can be appropriately set, it is formed to be slightly smaller than a diameter of 5 mm in the case of using a trocar having a diameter of 5 mm.

As shown in FIG. 3A, the inner tube 42 integrally includes a first tubular section 52, a diameter change section 54, and a second tubular section 56 from the distal end side toward the proximal end side. The first tubular section 52, the diameter change section 54, and the second tubular section 56 are symmetrically formed with respect to the central axis C.

Figure 3B:
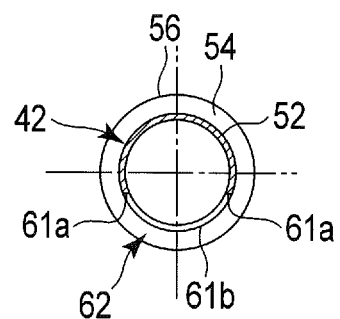
FIG. 3B is a schematic transverse cross-sectional view taken along a line of arrows 3B-3B in FIG. 3A.
Figure 3C:
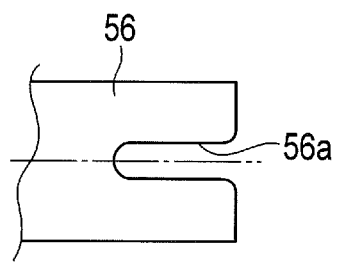
FIG. 3C is a schematic side view showing the inner tube of the sheath of the treatment device according to the first embodiment seen from a direction of an arrow 3C in FIG. 3A.

As shown in FIG. 1A and FIG. 1B, the first tubular section 52 is arranged at a position protruding with respect to the distal end of the handle 16 and has the same inner diameter and the same outer diameter. Openings 60 and 62 that enable the inner side to communicate with the outer side are formed in a side surface of the first tubular section 52. As shown in FIG. 3A and FIG. 3B, the openings 60 and 62 have, e.g., a pair of first edge portions 61*a* formed parallel to the axial direction of the central axis C and a pair of second edge portions 61*b* that are orthogonal to the axial direction of the central axis C and have opposed arc-like surfaces, respectively. The openings 60 and 62 are formed into the same shape and the same size. The opening 60 is formed at a position corresponding to the first node position of the vibration (a common axial position of the longitudinal axis L of the probe 12 and the central axis C of the sheath 14) on the proximal end side from the distal end of the first tubular section 52 in a state that the probe 12 is attached to the sheath 14 of the treatment device 10. The opening 62 formed separately from the opening 60 is formed at a position corresponding to the node position of the vibration between the position corresponding to the first node position of the vibration on the proximal end side from the distal end of the first tubular section 52 and the distal end of the handle 16. In particular, it is preferable for the opening 62 to be formed at a position corresponding to the first node position of the vibration from the distal end of the handle 16 on the distal end side (the common axial position of the longitudinal axis L of the probe 12 and the central axis C of the sheath 14). A description will be given as to a case where the opening 62 is formed at a position corresponding to the node position of the vibration between the first node position of the vibration on the proximal end side from the distal end of the first tubular section 52 and the first node position of the vibration on the distal end side from the distal end of the handle 16.

It is to be noted that a circumferential width (a width between the first edge portions 61*a*) of each of the openings 60 and 62 of the first tubular section 52 around the central axis C can be appropriately set, but it is, e.g., approximately 90° with respect to the central axis C. Additionally, an axial length of each of the openings 60 and 62 along the axial direction of the central axis C (a distance between the second edge portions 61*b*) can be appropriately set based on a relationship with the node position of the vibration of the probe 12, and it is, e.g., approximately several mm to 5 mm.

Figure 6B:
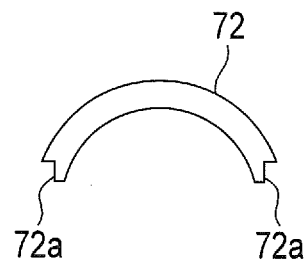
FIG. 6B is a schematic front view showing the arc-shaped body arranged through the opening depicted in FIG. 6A.
Figure 6C:
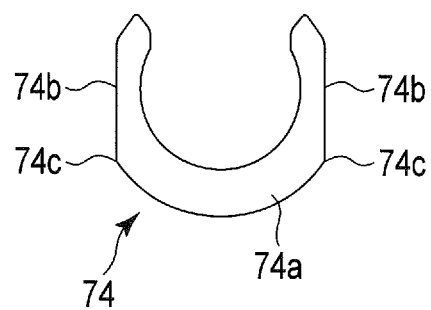
FIG. 6C is a schematic front view showing the support member arranged through the opening depicted in FIG. 6A.
Figure 7B:
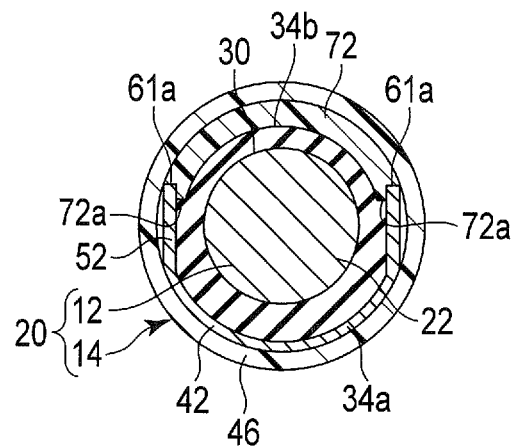
FIG. 7B is a schematic transverse cross-sectional view taken along a line of arrows 7B-7B in FIG. 7A.
Figure 7C:
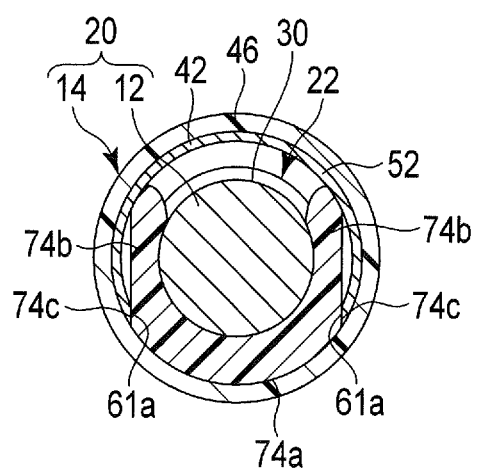
FIG. 7C is a schematic transverse cross-sectional view taken along a line of arrows 7C-7C in FIG. 7A.

The support member (a support section) 74 that supports the annular groove 30 of the probe 12 is arranged in each opening 62 in a state that the probe 12 is inserted in the inner tube 42. The support member 74 is formed into a size that enables insertion into each opening 62. As shown in FIG. 6A and FIG. 6B, an arc-shaped body (a support section) 72 made of a resin material is arranged in the first opening 60 formed from the distal end toward the proximal end side of the first tubular section 52 of the inner tube 42. As shown in FIG. 6A and FIG. 6C, a substantially U-shaped support member 74 made of the resin material is arranged in the first opening 62 formed toward the distal end side with respect to the distal end of the handle 16. The support member 74 includes an arc-shaped portion 74*a* and a pair of leg portions 74*b* integrally formed on the arc-shaped portion 74*a*. An inner peripheral surface of the arc-shaped portion 74*a* and opposed surfaces of the pair of leg portions 74*b* directly hold the outer peripheral surface of the annular groove 30 of the probe 12. A portion near a boundary between the arc-shaped portion 74*a* and each leg portion 74*b* is determined as a shoulder portion 74*c*.

It is also preferable for the support member 74 to support the annular groove 30 of the probe 12 through each opening 62 between the first opening 60 from the distal end toward the proximal end side of the first tubular section 52 of the inner tube 42 and the first opening 62 toward the distal end side with respect to the distal end of the handle 16. That is, it is preferable for the arc-shaped body 72 to be arranged in the opening 60 that is the first one on the proximal end side from the distal end of the first tubular section 52 of the inner tube 42 between the inner tube 42 of the sheath 14 and the annular groove 30 of the probe 12, and also preferable for each annular groove 30 to be supported by the support member 74 arranged through each opening 62.

When the openings 60 and 62 are formed in the inner tube 42, it is preferable to form the openings 60 and 62 at different angles along the circumferential direction relative to the central axis C. In particular, it is preferable for two of the openings 60 and 62 to be formed at positions where they face the central axis C. That is, for example, when a position of the opening 60 that is the first one on the proximal end side from the distal end of the inner tube 42 is a position of 0° with respect to the central axis C, it is preferable for a position of the opening 62 that is the first one on the distal end side from the distal end of the handle 16 to be a position of 180° relative to the central axis C. The position of the opening 62 that is the first one on the distal end side from the distal end of the handle 16 is not restricted to 180°, and it can be appropriately set to, e.g., 30°, 45°, or 60°. When the position of the opening 62 is deviated from the central axis C in this manner, the longitudinal axis L of the probe main body section 22 can be easily matched with the central axis C of the inner tube 42, and the matched state can be readily maintained. When the openings 62 are present, a relationship between the openings 62 is the same as above.

The diameter change section 54 is arranged between the first tubular section 52 and the second tubular section 56. The diameter change section 54 is spread in a flare shape from the distal end side toward the proximal end side to be symmetrical with respect to the central axis C. That is, the inner diameter and the outer diameter of the second tubular section 56 are larger than those of the first tabular section 52. The diameter change section 54 is inclined in a state that each angle α is substantially 30° with respect to an axis parallel to the central axis C. Further, the diameter change section 54 is arranged on the inner side of the distal end portion of the handle 16 to restrict the movement of the inner tube 42 toward the distal end side of the handle 16.

The second tubular section 56 is extended toward the proximal end side from the proximal end of the diameter change section 54 while maintaining the inner diameter and the outer diameter of the diameter change section 54 at the most proximal position. A pair of U-shaped grooves 56*a* (see FIG. 3C) each having a substantially U-like shape that face the central axis C are formed to the second tubular section 56 from the proximal end thereof toward the distal end side. A pin 96 (see FIG. 8) is arranged in each U-shaped groove 56*a* from the outer side toward the inner side of the later-described holder 84 of the handle 16 so that the sheath 14 is rotatable with respect to a later-described main body 82 of the handle 16. It is to be noted that arranging the pin 96 in each U-shaped groove 56*a* restricts the movement of the second tubular section 56, i.e., the sheath 14 toward the proximal end side.

The distal end pipe 44 shown in FIG. 4 is made of a resin material having insulation properties and heat-resisting properties such as a PTFE material. A slit 44a is formed on the distal end side of the distal end pipe 44 to be parallel to the central axis C, and the proximal end side of the distal end pipe 44 is circularly formed so that it can be fitted to the distal end of the first tubular section 52 of the inner tube 42. Since the slit 44a is formed, the asymmetrical portion 24a at the distal end of the treatment section 24 of the probe 12 can be passed from the distal end of the probe main body section 22 (the proximal end of the treatment section 24). The distal end pipe 44 includes a contact portion 44b which contacts on the distal end of the first tubular section 52 of the inner tube 42 and a contact portion 44c which contacts on the distal end of the outer tube 46.

The distal end pipe 44 is formed to be more tapered toward the distal end side than the distal ends of the inner tube 42 and the outer tube 46. That is, an area of a transverse cross section of the distal end pipe 44 on the inner side at the outermost periphery thereof is gradually reduced from the proximal end side toward the distal end side. Further, at least part of the distal end pipe 44 is formed in such a manner that the area of the transverse cross section of the distal end pipe 44 on the inner side at the outermost periphery thereof is smaller than that of a transverse cross section of the probe main body section 22. Therefore, when the distal end pipe 44 is arranged at the distal ends of the inner tube 42 and the outer tube 46, visibility in a treatment region can be improved at the time of visually confirming the treatment region of a biological tissue by using a non-illustrated endoscope (a rigid scope) in, e.g., a laparoscopic surgery operation.

It is to be noted that a description will be given on the assumption that the distal end pipe 44 made of a resin material is arranged at the distal end of the first tubular section 52 of the inner tube 42, but the distal end pipe 44 does not have to be arranged at the distal end of the first tubular section 52 of the inner tube 42.

In a state that the distal end pipe 44 is arranged at the distal end of the inner tube 42 and the arc-shaped body 72 is arranged in the opening 60 of the first tubular section 52 while the support member 74 is arranged in each opening 62 of the same, the outer tube 46 covers the entire circumference from the distal end of the inner tube 42 to a position near the distal end of the diameter change section 54. It is to be noted that the inner tube 42 and the outer tube 46 are integrated.

Figure 8:
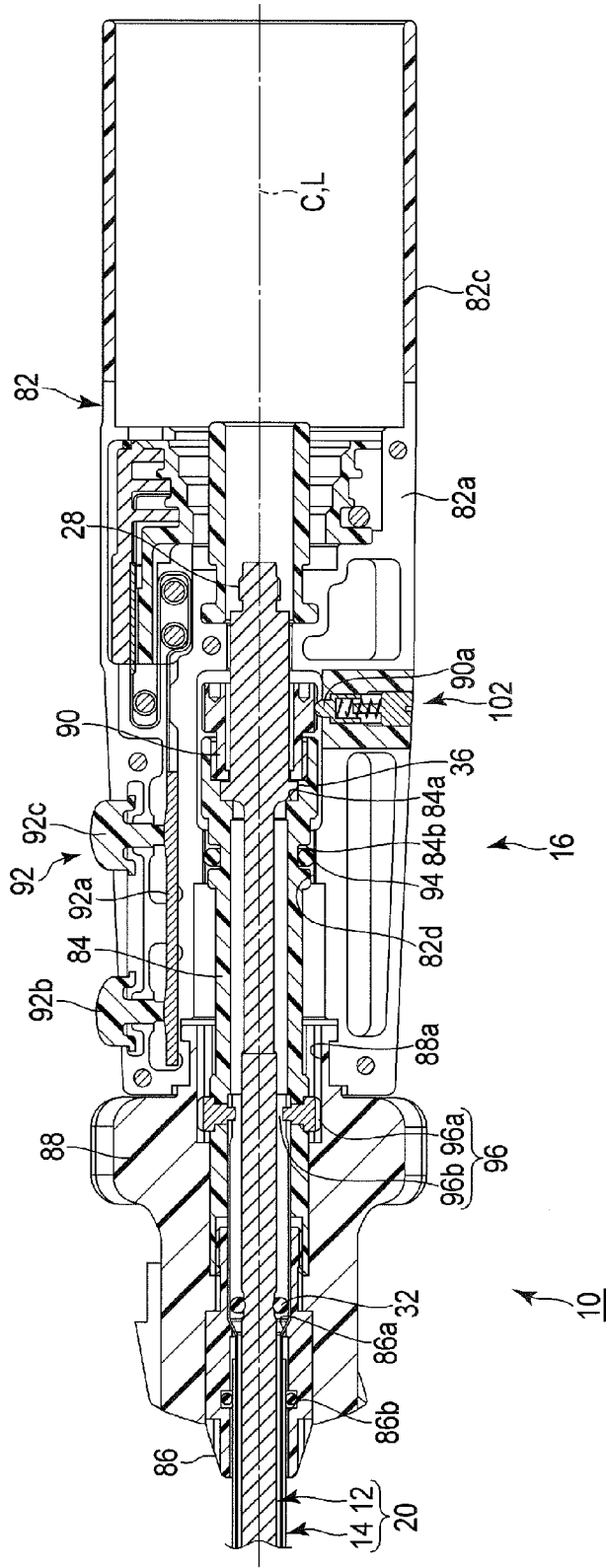
FIG. 8 is a schematic longitudinal cross-sectional view showing a state that the treatment assembly of the treatment device according to the first embodiment is attached to a handle.

As shown in FIG. 1A, FIG. 1B, and FIG. 8, the handle 16 includes a main body (a grip section) 82, a cylindrical holder 84 that supports the probe 12, a sheath presser 86, a rotation knob 88, and the fixing member 90. The main body 82, the holder 84, the sheath presser 86, the rotation knob 88, and the fixing member 90 have the same central axis as the central axis C of the sheath 14.

The main body 82 of the handle 16 includes a first main body 82a shown in FIG. 1A and FIG. 8 and a second main body 82b that is used as a lid and shown in FIG. 1B. The holder 84, the sheath presser 86, the rotation knob 88, and the fixing member 90 can be fitted to the main body 82, i.e., the first main body 82a and the second main body 82b. Furthermore, an attachment section 82c to which the ultrasonic transducer unit 18 shown in FIG. 1A is attached is formed on the first main body 82a. A switch mechanism 92 that switches a state that input of energy such as ultrasonic vibration energy or high-frequency energy to the probe 12 is stopped to an input state when the ultrasonic transducer unit 18 is being attached to the attachment section 82c is further arranged on the first main body 82a. It is to be noted that, in this embodiment, the switch mechanism 92 includes a substrate 92a, a cut mode switch 92b, and a coagulation mode switch 92c that enables inputting the ultrasonic vibration energy or the high-frequency energy to the probe 12 when pressed. The cut mode switch 92b and the coagulation mode switch 92c are arranged on the substrate 92a. When the cut mode switch 92b is pressed, the high-frequency energy is input to the probe 12. When the coagulation mode switch 92c is pressed, the ultrasonic vibration energy and the high-frequency energy are input to the probe 12.

As shown in FIG. 8, when the probe 12 is arranged at a predetermined position of the treatment device 10, the holder 84 covers the outer periphery of the proximal end portion of the probe 12. The holder 84 has a fitting section 84a that is fitted while locking the fitting section 36 (se FIG. 2A and FIG. 2B) of the probe 12. A concave portion 84b in which an O-ring 94 is arranged is formed on an outer peripheral surface of the holder 84. It is to be noted that a pressing section 82d that presses the O-ring 94 and gives a sliding resistance force when the holder 84 rotates with respect to the main body 82 is formed on an inner peripheral surface of the main body 82. At this time, the sliding resistance force when the holder 84 rotates with respect to the main body 82 is smaller than 1 Nm. For example, it is preferable for the sliding resistance force to be, e.g., approximately 0.1 Nm to 0.5 Nm. Therefore, a circumferential position of the probe 12 relative to the main body 82 of the handle 16 can be finely adjusted around the central axis C. The probe 12 can be prevented from involuntarily rotating around the central axis C with respect to the main body 82 due to gravity and the like.

A pair of pins 96 facing the central axis C are arranged on the holder 84. A head portion 96a of each pin 96 is provided on the outer side of the holder 84, and a distal tip 96b of a shaft portion of the pin 96 relative to the head portion 96a is provided on the inner side of the holder 84.

The sheath presser 86 is supported at the distal end of the holder 84 and arranged on the inner side of the rotation knob 88. The sheath presser 86 has an inclined surface 86a, which supports the outer peripheral surface of the diameter change section 46 of the sheath 14, on the inner peripheral surface thereof. Therefore, falling of the sheath 14 to the distal end side of the handle 16 is regulated.

A concave portion 86b in which an O-ring 98 is arranged is formed on the inner peripheral surface of the sheath presser 86 between this surface and the outer peripheral surface of the sheath 14, i.e., the outer peripheral surface of the outer tube 46. Therefore, a leak current or a breakdown voltage is strongly achieved between the outer peripheral surface of the outer tube 46 of the sheath 14 and the inner peripheral surface of the sheath presser 86.

The rotation knob 88 is arranged on the outer side of the holder 84 and the sheath presser 86. The rotation knob 88 includes a pair of concave grooves 88a into which the head portions 96a of the pins 96 arranged on the holder 84 are fitted. Therefore, when the rotation knob 88 is operated to rotate around the central axis C, rotational force can be given to the holder 84 through the pins 96.

The fixing member 90 is arranged at the proximal end of the holder 84 and supports the probe 12 in a fixed state when the probe is rotation-locked with respect to the holder 84. Click engagement sections 90a that are engaged with a click mechanism 102 arranged in the main body 82 are formed on the outer peripheral surface of the fixing member 90. When the rotation knob 88 is rotated, the fixing member 90 rotates with respect to the click mechanism 102 through the pins 96 and the holder 84, and a clicking sound is generated at the time of arranging each adjacent click engagement section 90a between the click mechanism 102 and the central axis C.

It is to be noted that using a material that is elastically deformable and has heat-resisting properties such as a PTFE material for the fixing member 90 is preferable. Furthermore, in the case of allowing a high-frequency current to flow through the probe 12, the fixing member 90 is made of a material having electric insulation properties such as a resin material for prevention of electric shock.

A description will now be given as to a procedure of attaching the probe 12 to the sheath 14 to manufacture the treatment assembly 20 used for a treatment of a biological tissue (a manufacturing method) according to this embodiment and an example of a procedure of attaching the handle 16 to this treatment assembly 20 to manufacture the treatment device 10 (a manufacturing method).

The distal end of the probe 12 shown in FIG. 2A is arranged to face the proximal end of the inner tube 42 having the openings 60 and 62 shown in FIG. 3A. It is to be noted that the annular body 34 is arranged in the annular groove 30 that is the first one from the distal end of the probe 12 on the proximal end side in advance. The treatment section 24 of the probe 12 is asymmetrically formed with respect to the longitudinal axis L of the probe main body section 22. Therefore, as shown in FIG. 4, in a state that the longitudinal axis L of the probe main body section 22 deviates from the central axis C of the inner tube 42, the probe 12 is inserted into the inner tube 42 toward the distal end from the proximal end. Moreover, the treatment section 24 of the probe tube 12 is protruded on the distal end side with respect to the distal end of the inner tube 42. At this time, as shown in FIG. 1A, FIG. 1B, and FIG. 8, the horn 26 of the probe 12 is provided on the proximal end side of the proximal end of the inner tube 42.

It is to be noted that, for example, the fitting section 36 of the horn 26 of the probe 12 is formed to be larger than the inner diameter of the first tubular section 52 of the inner tube 42. Specifically, a distance from the central axis C of the horn 26 to the distal tip of the fitting section 36 is larger than a radius of the inner diameter of the first tubular section 52 of the inner tube 42. Therefore, the probe 12 cannot be inserted into the inner tube 42 from the proximal end toward the distal end from a state that the horn 26 of the probe 12 is facing the distal end of the inner tube 42.

Figure 5:
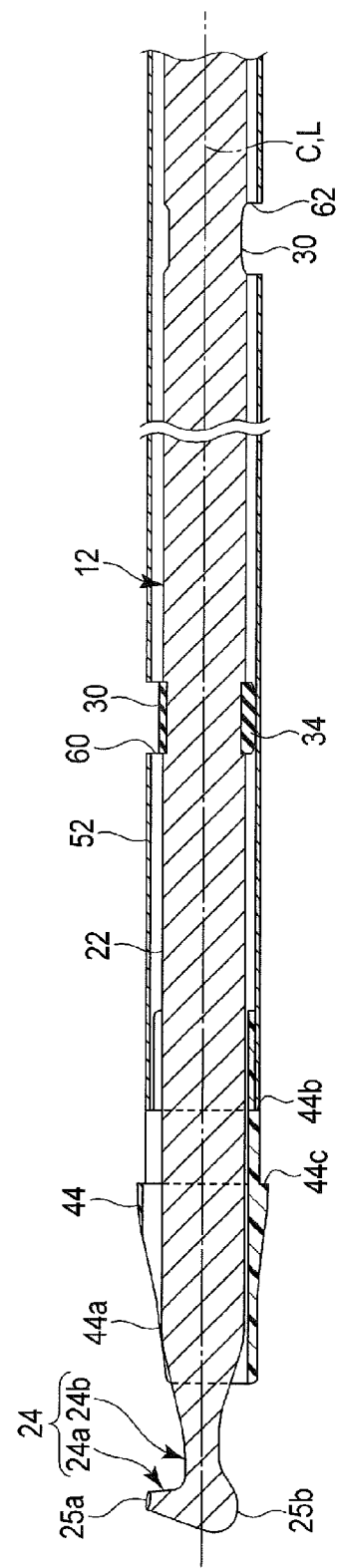
FIG. 5 is a schematic longitudinal cross-sectional view showing a state that the probe is inserted from the proximal end side toward the distal end side of the inner tube of the sheath of the treatment device according to the first embodiment and the distal end pipe is likewise inserted and also showing a state that the distal end pipe is arranged at the distal end of the inner tube.

Here, the treatment section 24 of the probe 12 is protruded toward the distal end side with respect to the distal end of the distal end pipe 44 from the proximal end side of the distal end pipe 44 shown in FIG. 4 through the slit 44a. Additionally, as shown in FIG. 5, the distal end of the inner tube 42 is arranged to contact on the contact portion 44b of the distal end pipe 44.

The openings 60 and 62 of the inner tube 42 are formed at positions corresponding to the node positions of the vibration from the distal end toward the proximal end side of the inner tube 42 in a state that the probe 12 is passed through the sheath 14. As shown in FIG. 5, the annular grooves 30 on the probe 12 are matched with the axial positions of the openings 60 and 62 of the inner tube 42, respectively. In this state, the arc-shaped body 72 shown in FIG. 6B is inserted into the opening 60 that is the first one from the distal end of the inner tube 42 on the proximal end side, and the engagement section 72a of the arc-shaped body 72 is engaged with the first edge portion 61a of the opening 60 of the inner tube 42. Therefore, the arc-shaped body 72 is appressed against the outer periphery of the arc-shaped concave portion 34b. It is to be noted that, when the engagement section 72a of the arc-shaped body 72 is engaged with the first edge portion 61a of the opening 60 of the inner tube 42, the longitudinal axis L of the probe main body section 22 coincides with the central axis C of the inner tube 42.

When the handle 16 is arranged on the outer side of the diameter change section 54 and the second tubular section 56 of the inner tube 42 of the sheath 14, the support member 74 shown in FIG. 6C is inserted into the opening 62 that is the first one on the distal end side with respect to the distal end of the handle 16, and the leg portions 74b of the support member 74 are arranged to contact on the inner peripheral surface of the inner tube 42. Therefore, the annular groove 30 is held on the inner peripheral surface of the arc-shaped portion 74a and the inner peripheral surfaces of the leg portions 74b of the support member 74. At this time, the shoulder portion 74c of the support member 74 is appressed against or has a slight gap with respect to each edge portion 61a of the opening 62, and revolving motion of the support member 74 around the central axis C with respect to the first tubular section 52 is regulated. It is to be noted that, when the support member 74 is arranged in each annular groove 30 on the probe 12 through the opening 62 of the inner tube 42, the longitudinal axis L of the probe main body section 22 is matched with the central axis C of the inner tube 42.

It is to be noted that, when one or more openings 62 are further present between the opening 60 in which the arc-shaped body 72 is arranged and the opening 62 in which the support member 74 is arranged, i.e., when the annular grooves 30 (the node positions of the vibration) on the probe 12 are present, the support member 74 is press-fitted into and arranged through each opening 62 of the first tubular section 52 as described above.

At this time, the outer peripheral surface of the arc-shaped body 72 and the outer peripheral surface of the support member 74 are substantially flush with the outer peripheral surface of the first tubular section 52 of the inner tube 42.

In this state, as shown in FIG. 7A, the outer tube 46 such as a heat shrinkable tube that shrinks when heated is put on the outer side of the inner tube 42. For example, the outer tube 46 is placed to be appressed against the entire circumference from the distal end of the first tubular section 52 of the inner tube 42 to a position near the distal end of the diameter change section 54. That is, air-tightness and liquid-tightness are achieved between the outer peripheral surface of the first tubular section 52 of the inner tube 42 and the inner peripheral surface of the outer tube 46. At this time, the proximal end side of the outer periphery of the distal end pipe 4 is also covered. Therefore, the arc-shaped body 72 engaged with the opening 60 can be appressed against the outer peripheral surface of the annular body 34 and held in this state, and the support member 74 arranged through the opening 62 can be fixed while supporting the annular groove 30 of the probe 12. Therefore, the arc-shaped body 72 arranged through the opening 60 of the inner tube 42 and the support member 74 arranged through the opening 62 are fixed by the outer tube 46, and the arc-shaped body 72 and the support member 74 are prevented from coming off the openings 60 and 62.

Here, of each leg portion 74b of the support member 74, the outer side of the distal tip relative to the arc-shaped portion 74a contacts on the inner peripheral surface of the inner tube 42. Therefore, opening of the leg portions 74b of the support member 74 is regulated. Further, the leg portions 74b of the support member 74 are arranged in the annular groove 30. Therefore, movement of the probe 12 in the axial direction with respect to the support member 74 is regulated. That is, the sheath 14 and the probe 12 are fixed in a state that the probe 12 is inserted into the sheath 14.

Furthermore, when the arc-shaped body 72 engaged in the opening 60 is appressed against the outer peripheral surface of the annular body 34 and held in this state, air-tightness and liquid-tightness are achieved not only between the outer peripheral surface of the probe main body section 22 and the annular body 34 but also between the annular body 34 and the arc-shaped body 72 and between the arc-shaped body 72 and the inner peripheral surface of the first tubular section 52 of the inner tube 42. Therefore, a liquid such as a biological fluid from a biological tissue or a normal saline solution and a gas such as carbon dioxide used for pneumoperitoneum that has flowed from a part between the inner peripheral surface of the first tubular section 52 of the inner tube 42 and the outer peripheral surface of the probe main body section 22 can be prevented from moving toward the proximal end side of the opening 60 provided at the most distal end of the inner tube 42 from the treatment section 24 and the slit 44a of the distal end pipe 44.

It is to be noted that, as shown in FIG. 7A, the distal tip 25a of the treatment section 24 is formed at a position close to the central axis C apart from a broken line DL virtually extended on the distal end side along the outer peripheral surface of the sheath 14 provided at a position where the outer tube 46 covers the outer side of the first tubular section 52.

As described above, the treatment assembly (an assembly of the probe 12 and the sheath 14) 20 used for a treatment of a biological tissue is manufactured.

The treatment assembly 20 in this state is inserted from the proximal end side toward the distal end side of the holder 84 of the handle 16. The fitting section 36 of the proximal end portion of the probe 12 is fitted while being locked to the fitting section 84a of the holder 84, and the outer peripheral surface of the diameter change section 54 of the sheath 14 is arranged to contact on the inclined surface 86a of the sheath presser 86. Additionally, the fixing member 90 is arranged on the proximal end side of the holder 84, the probe 12 is positioned with respect to the holder 84, and the sheath 14 is positioned with respect to the sheath presser 86. In this embodiment, a position of the distal end of the fixing member 90 corresponds to the node position of the vibration of the probe 12.

The O-ring 94 is arranged in the concave portion 84b on the outer peripheral surface of the holder 84.

The pin 96 is arranged in each U-shaped groove 56a of the second tubular section 56 of the sheath 14 from the outer side of the distal end portion of the holder 84. At this time, the end portion 96b of each pin 96 close to the central axis C is placed at a position apart from the outer peripheral surface of the probe 12. Further, the rotation knob 88 is attached to the outer side of the holder 84 and the sheath presser 86 while arranging each pin 96 in the concave groove 88a on the inner side of the rotation knob 88.

In this state, the holder 84 which protrudes the proximal end portion of the probe 12 on the proximal end side of the holder 84 and the rotation knob 88 which protrudes the proximal end portion of the holder 84 on the proximal end side of the rotation knob 88 are arranged on the first main body 82a of the handle 16. The first main body 82a is covered with the second main body 82b.

The treatment device 10 is manufactured by, e.g., such a procedure.

The ultrasonic transducer unit 18 is connected to the proximal end of the handle 16 of the treatment device 10 and used. When the ultrasonic transducer 18a of the ultrasonic transducer unit 18 ultrasonically vibrates, vertical vibration from the ultrasonic transducer 18a connected to the proximal end of the probe 12 is transferred from the proximal end of the probe 12 toward the treatment section 24 at the distal end portion. At this time, the central axis C of the ultrasonic transducer 18a is matched with the longitudinal axis L of the probe 12, a node position of vibration at, e.g., the most distal end is supported, and hence the vibration is transferred to the treatment section 24 in a state that the irregular vibration is avoided. Therefore, an appropriate treatment can be given by the treatment section 24 using the ultrasonic vibration.

In the case of using the treatment device 10 for laparoscopic surgery through a non-illustrated trocar, the treatment section 24 is inserted into the trocar. The trocar is held at an appropriate position between the distal end and the proximal end of the sheath 14, and a treatment is given to a biological tissue. At this time, since the O-ring 32 is arranged between the outer peripheral surface of the probe 12 and the inner peripheral surface of the sheath 14, a gas (carbon dioxide) can be prevented from flowing out of an abdominal region through a part between the probe 12 and the sheath 14. Further, the annular body 34, the arc-shaped body 72, the inner peripheral surface of the first tubular section 52 of the inner tube 42, and the outer tube 46 can prevent the gas (the carbon dioxide) from flowing out of the abdominal region through the part between the probe 12 and the sheath 14.

As described above, according to this embodiment, the following can be said.

At the time of inserting the probe 12 into the inner tube 42, the treatment section 24, in which a distance between the end portions 25a and 25b is equal to or slightly smaller than a minimum inner diameter of the inner tube 42, can be inserted into the inner tube 42. At the time, the insertion is effected in a state that the longitudinal axis L of the probe 12 is slightly deviated from the central axis C of the inner tube 42. Therefore, even if the distance L1 between the longitudinal axis L of the probe 12 and the distal tip 25a of the treatment section 24 of the probe 12 is larger than a distance between the central axis C of the sheath 14 and the inner peripheral surface of the inner tube 42 (a radius of the first tubular section 52 of the inner tube 42), the treatment section 24 of the probe 12 can be protruded with respect to the distal end of the sheath 14.

That is, it is possible to provide the treatment device 10 that enables inserting the probe 12 into the sheath 14 even if the distal end portion of the probe 12, i.e., the treatment section 24 has a shape protruding toward the outer side with respect to the inner peripheral surface of the sheath 14 when the probe 12 is inserted into the sheath 14 and the central axis C of the sheath 14 is matched with the longitudinal axis L of the probe 12, and provide the manufacturing method of the treatment device 10.

Therefore, to conduct, e.g., laparoscopic surgery, when pneumoperitoneum is performed and the treatment section 24 of the probe 12 of the treatment device 10 and the distal end portion of the sheath 14 are inserted into a body cavity through a non-illustrated trocar, the distance L1 from the longitudinal axis L to the distal tip 25a in the treatment section 24 can be increased. Therefore, an operation for catching a biological tissue can be easily carried out with respect to a conventional treatment device in which a distance from the longitudinal axis L to the distal tip is shorter. That is, in the treatment device 10 to which the probe 12 is attached through the sheath 14, since the treatment section 24 can be formed to be larger than that in a conventional example, easiness of giving a treatment to the biological tissue can be greatly improved.

It is to be noted that, in this embodiment, the description has been given as to the example where the annular body 34 is arranged in the annular groove 30 at the node position of the vibration on the most distal end side of the probe 12 in advance and the arc-shaped body 72 is arranged on the outer periphery of the annular body 34 through the opening 60. However, the annular body 34 does not have to be arranged in the annular groove 30 at the node position of the vibration on the most distal end side of the probe 12 in advance. The same support member 74 as the support member 74 arranged in the annular groove 30, which is the first one on the distal end side from the distal end of the handle 16, through the opening 62 can be arranged through the opening 60. That is, in place of arranging the arc-shaped body 72, the support member 74 may be arranged in the annular groove 30 at the node position of the vibration on the most distal end side of the probe 12 through the opening 60 provided on the most distal end side of the sheath 14. Even in this case, the O-ring 32 arranged between the outer peripheral surface of the probe main body section 22 and the inner peripheral surface of the second tubular section 56 of the inner tube 42 of the sheath 14 can prevent a gas and a liquid from flowing from the distal end side toward the proximal end side of the O-ring 32.

In this embodiment, as shown in FIG. 6C, although the description has been given as to the example where the pair of leg portions 74b are extended by the same length from the arc-shaped portion 74a and symmetrically formed, it is also preferable to asymmetrically form the pair of leg portions 74b with different lengths.

In this embodiment, the description has been given as to the case that the openings 60 and 62 formed in the side surface of the inner tube 42 of the sheath 14 have the same shape and size, but forming the openings 60 and 62 into different shapes is also possible, and forming the openings 60 and 62 in different sizes is also possible.

Figure 9A:
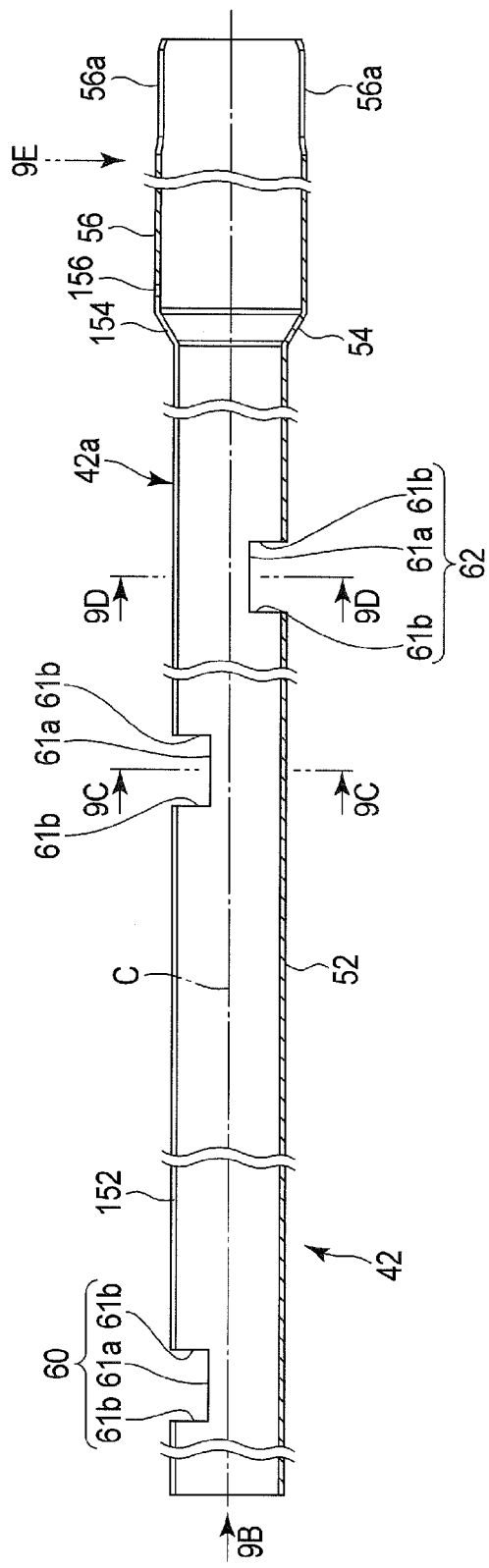
FIG. 9A is a schematic longitudinal cross-sectional view showing an inner tube of a sheath of a treatment device according to a second embodiment.
Figure 9B:
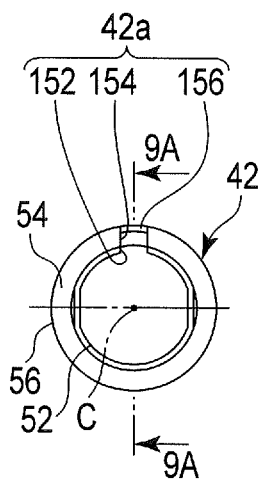
FIG. 9B is a schematic front view showing the inner tube of the treatment device according to the second embodiment from a direction of an arrow 9B in FIG. 9A.
Figure 9C:
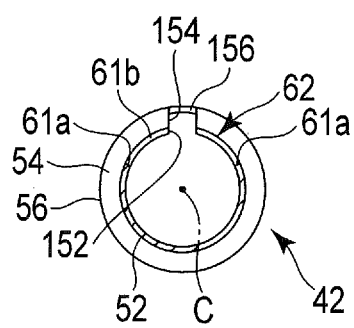
FIG. 9C is a schematic transverse cross-sectional view taken along a line of arrows 9C-9C in FIG. 9A.
Figure 9D:
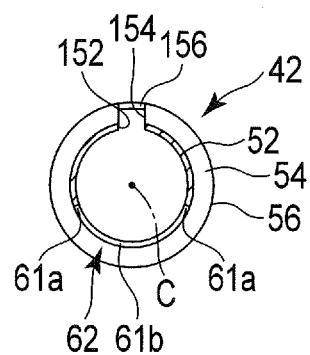
FIG. 9D is a schematic transverse cross-sectional view taken along a line of arrows 9D-9D in FIG. 9A.
Figure 9E:
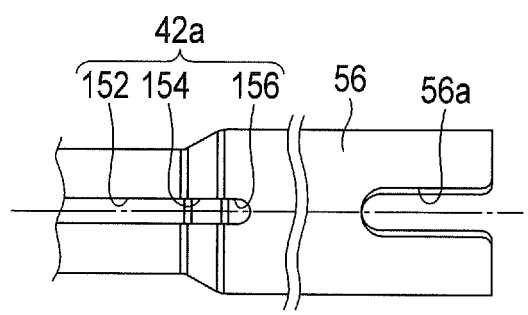
FIG. 9E is a schematic side view showing a state seen from a direction of an arrow 9E in FIG. 9A.

A second embodiment will now be described with reference to FIG. 9A to FIG. 10. This embodiment is a modification of the first embodiment, and like reference signs denote members equal to the members described in the first embodiment or members having the same functions as much as possible, thereby omitting a detailed description thereof.

This embodiment is a modification of the inner tube 42 of the sheath 14 explained in the first embodiment.

As shown in FIG. 9A to FIG. 9E, a slit 42a parallel to the central axis C is formed from the distal end toward the proximal end of the first tubular section 52 of the inner tube 42 and from the distal end toward the proximal end of the diameter change section 54. It is preferable for a proximal end of the slit 42a to be extended to the distal end portion of the second tubular section 56. That is, the slit 42a of the inner tube 42 is obtained by integrally forming a first slit 152 formed in the first tubular section 52, a second slit 154 formed in the diameter change section 54, and a third slit 156 formed in the second tubular section 56. The slit 42a is closed with a proximal end of the third slit 156. It is to be noted that a width of the slit 42a can be appropriately set, but maintaining the same state from the distal end toward the proximal end of the slit 42a is preferable. It is preferable to avoid increasing the width of the slit 42 beyond necessity if the width is formed to enable passing through the treatment section 24 of the probe 12.

When the inner tube 42 according to this embodiment is used, in the treatment section 24 of the probe 12, a distance L1a larger than the distance L1 explained in the first embodiment can be set. Therefore, for example, a portion to catch a biological tissue can be further enlarged as compared with the case described in the first embodiment.

Since other structures and functions of the treatment device 10 are the same as those explained in the first embodiment, a description will be omitted here.

Figure 10:
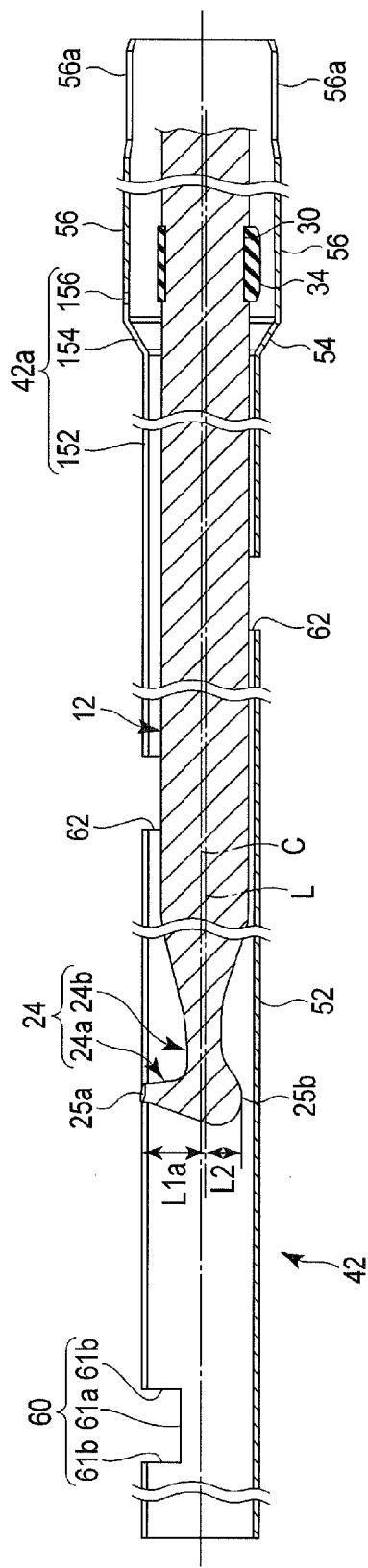
FIG. 10 is a schematic longitudinal cross-sectional view showing a state that a probe is inserted from a proximal end side toward a distal end side of an inner tube of a sheath of a treatment device according to a second embodiment.

It is to be noted that the treatment section 24 of the probe 12 according to this embodiment is formed to be larger on the upper side of the longitudinal axis L in FIG. 10 than the treatment section 24 (see FIG. 7A) described in the first embodiment, but it is preferable to form the treatment section 24 in such a manner that a distal tip 25a of the treatment section 24 can be provided on a broken line DL shown in FIG. 7A. In this case, the treatment device 10 according to this embodiment can be used for a treatment that is given through a trocar slightly larger than the outer diameter of the sheath 14 at a position where the outer tube 46 is put on the outer side of the first tubular section 52.

Reference cases relating to the treatment device 10 described in each of the first and second embodiments will now be explained with reference to FIG. 11 to FIG. 15B.

Figure 11:
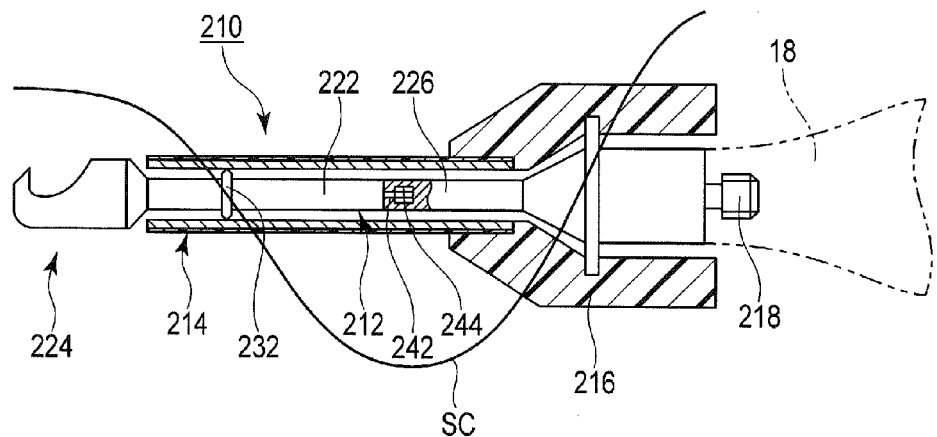
FIG. 11 is a schematic partial longitudinal cross-sectional view showing a treatment device according a first reference case.

A first reference case will now be described with reference to FIG. 11. It is to be noted that FIG. 11 shows a sine curve SC of ultrasonic vibration superimposed on a treatment device 210 according to the first reference case.

The treatment device 210 according to the first reference case includes a probe 212, an elongated sheath 214 into which the probe 212 is inserted, and a holding section (an operating section) 216 arranged at a proximal end of the sheath 214. The sheath 214 has an inner tube made of, e.g., a stainless steel material and an outer tube made of a resin material or the like having insulation properties. It is to be noted that the outer tube covers an inner peripheral surface of a distal end portion of the inner tube. The holding section 216 is made of, e.g., a resin material. As described above, the ultrasonic transducer unit 18 that is connected to the ultrasonic vibration energy source (not shown) and has the ultrasonic transducer 18a that gives the probe 212 ultrasonic vibration energy can be attached to or detached from the treatment device 210 according to this reference case.

The probe 212 includes a probe main body section (a shaft) 222, a treatment section (a probe distal end portion) 224 that is provided on the distal end direction side of the probe main body section 222 and configured to give a biological tissue a treatment, and a horn (a probe proximal end portion) 226 that is provided on a proximal end direction side of the probe main body section 222 and configured to increase an amplitude of the ultrasonic vibration. It is to be noted that a coupling section (a screw section) 228 is formed at a proximal end of the probe 212. The coupling section 228 at the proximal end of the probe 212 can be attached to or detached from the coupling section 18c at the distal end of the fixing member 18b fixed to the ultrasonic transducer 18a shown in FIG. 1A.

It is to be noted that the probe main body section 222 and the treatment section 224 are made of, e.g., a titanium alloy, and the horn 226 is made of various kinds of duralumin including an aluminum alloy or the like.

An outer diameter of the probe main body section 222 is smaller than an inner diameter of the sheath 214. The treatment section 224 is formed to be larger than, e.g., an inner diameter of a distal end of the sheath 214. However, it is preferable for a distance between an outer side of the treatment section 224 in a radial direction and a longitudinal axis L to be equal to or smaller than a distance between an outer peripheral surface of the sheath 14 and a central axis C. Therefore, the treatment section 224 and the sheath 214 can be inserted into a body cavity or the like by using a trocar (not shown) formed to be slightly larger than an outer diameter of the sheath 214.

An O-ring 232 is arranged on an outer peripheral surface of the probe main body section 222 at a position corresponding to a node position of vibration of the ultrasonic vibration to support the probe 214 at a predetermined position with respect to the sheath 214. This O-ring 232 is made of, e.g., a PTFE material having electric insulation properties and heat-resisting properties.

A proximal end of the probe main body section 222 and a distal end of the horn 226 can be attached to or detached from each other through coupling sections 242 and 244 such as screw sections. It is to be noted that the coupling sections 242 and 244 are provided at positions corresponding to anti-node positions of the vibration.

The horn 226 is held by a holding section (an operating section) 216 at a position corresponding to the node position of the vibration.

The treatment device 210 according to the first reference case attaches the coupling section 242 of the probe main body section 222 to the coupling section 244 of the horn 226 in a state that the sheath 214 is connected to the holding section 216 and the horn 226 is attached to the holding section 216. At this time, since the treatment section 224 does not have to be inserted in the sheath 214, at least part of the treatment section 224 can be formed to be larger than the inner diameter of the sheath 214.

It is to be noted that the O-ring 232 is arranged on the inner peripheral surface of the sheath 14, and hence a gas can be prevented from flowing out of an abdominal region through a portion between the probe 212 and the sheath 214.

Figure 12A:
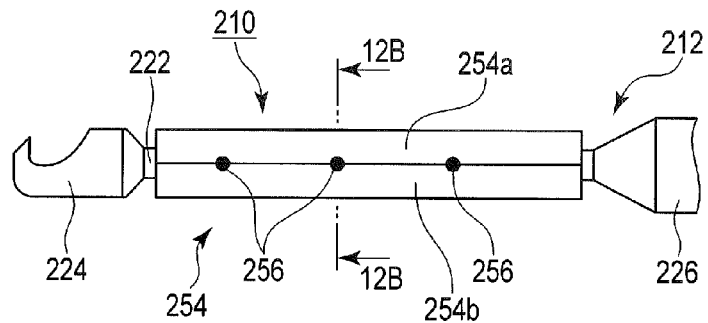
FIG. 12A is a schematic side view showing a treatment device according to a second reference case.
Figure 12B:
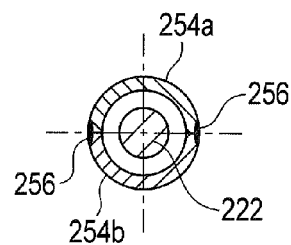
FIG. 12B is a schematic transverse cross-sectional view taken along a line of arrows 12B-12B in FIG. 12A, showing the treatment device according to the second reference case.

A second reference case will now be described with reference to FIG. 12A and FIG. 12B. This reference case is a modification of the first reference case.

In this reference case, differing from the probe 212 in the first reference case, the coupling sections 242 and 244 do not have to be present.

A sheath 254 of the treatment device 210 according to the second reference case has a first half-pipe 254a and a second half-pipe 254b each having a semicircular transverse cross section. The first half-pipe 254a and the second half-pipe 254b are made of a metal material. Divided end faces of the first half-pipe 254a and the second half-pipe 254b are arranged to contact on each other, and these half-pipes are fixed by, e.g., laser welding in this state. That is, end portions of the first half-pipe 254a and the second half-pipe 254b are fixed at welding portions 256.

It is to be noted that, for example, a non-illustrated O-ring is arranged between the sheath 254 and a probe main body section 222 so that the probe 212 and the sheath 254 are separated from each other. Further, although not shown, an outer peripheral surface of the sheath 254 is covered with a tube having insulation properties.

Figure 13:
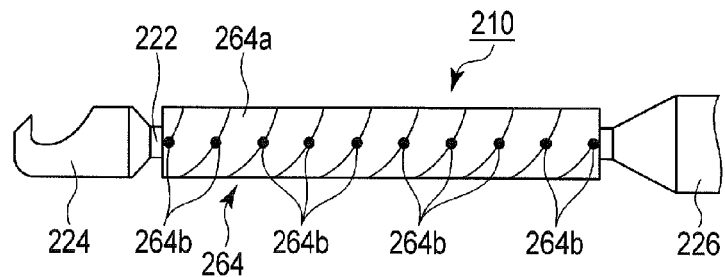
FIG. 13 is a schematic side view showing a treatment device according to a third reference case.

A third reference case will now be described with reference to FIG. 13. This reference case is a modification of the first and second reference cases. In particular, this reference case is a modification of the second reference case.

In a sheath 264 of a treatment device 210 according to the third reference case, a strip-shaped member 264a made of a metal material is wound around an outer peripheral surface of a probe main body section 222 to be formed into a coil pipe shape. In the strip-shaped member 264a, part or all of end portions arranged to abut on each other are fixed by, e.g., laser welding. That is, the end faces of the strip-shaped member 264a are fixed at welding portions 264b.

It is to be noted that, for example, a non-illustrated O-ring is arranged between the sheath 264 and the probe main body section 222 so that the probe 212 is separated from the sheath 264. Moreover, although not shown, the outer peripheral surface of the sheath 264 is covered with a tube having insulation properties.

Figure 14A:
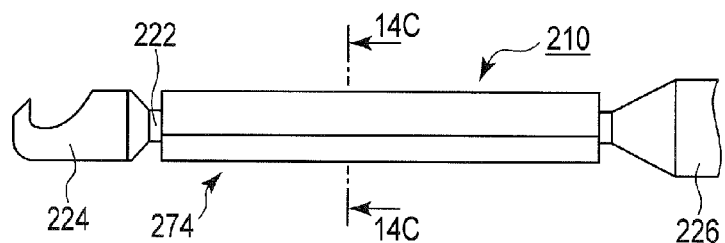
FIG. 14A is a schematic side view showing a treatment device according to a fourth reference case.
Figure 14B:
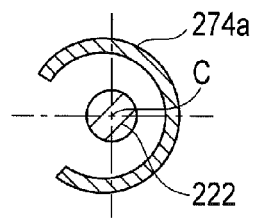
FIG. 14B is a schematic transverse cross-sectional view taken along a line of arrows 14C-14C in FIG. 14A, showing a state that a probe main body portion of a treatment device according to the fourth reference case is covered with a probe main body section.
Figure 14C:
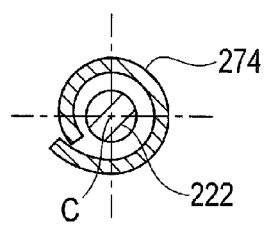
FIG. 14C is a schematic transverse cross-sectional view taken along a line of arrows 14C-14C in FIG. 14A, showing a treatment device according to the fourth reference case.

A fourth reference case will now be described with reference to FIG. 14A to FIG. 14C. This reference case is a modification of the first to third reference cases. In particular, this reference case is a modification of the second and third reference cases.

A sheath 274 of a treatment device 210 according to the fourth reference case is formed into a pipe shape by swaging a metallic member having a substantially C-like transverse cross section. A distance between end portions of a sheath forming body 274a shown in FIG. 14B is formed to be larger than an outer diameter of a probe main body section 222. When the sheath forming body 274a shown in FIG. 14B is swaged in this state as depicted in FIG. 14C, the sheath 274 is formed.

It is to be noted that, for example, an O-ring is arranged between the sheath 274 and the probe main body section 222 so that the probe 212 is separated from the sheath 274. Additionally, although not shown, an outer peripheral surface of the sheath 274 is covered with a tube having insulation properties.

According to the first to fourth reference cases, the treatment section 224 is formed to be larger than the inner diameter of the distal end of each of the sheaths 214, 254, 264, and 274 in all the reference cases. However, a distance between the outer side of the treatment section 224 in the radial direction and the longitudinal axis L of the probe 212 is substantially equal to a distance between the outer peripheral surface of the sheath 214 and the central axis C. Therefore, the treatment section 224 and the sheath 214 can be inserted into, e.g., a body cavity by using a trocar (not shown) formed to be slightly larger than the outer diameter of the sheath 214. Additionally, since the treatment section 224 can be formed to be larger as compared with a case where the treatment section 224 is attached through the inner diameter of the sheath, easiness of giving a treatment to a biological tissue can be greatly improved.

Figure 15A:
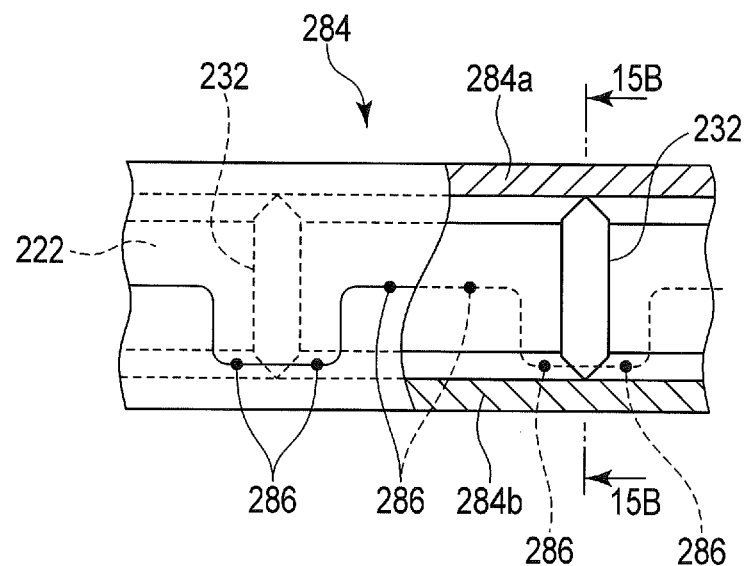
FIG. 15A is a schematic partial longitudinal cross-sectional view showing a treatment device according to a fifth reference case.
Figure 15B:
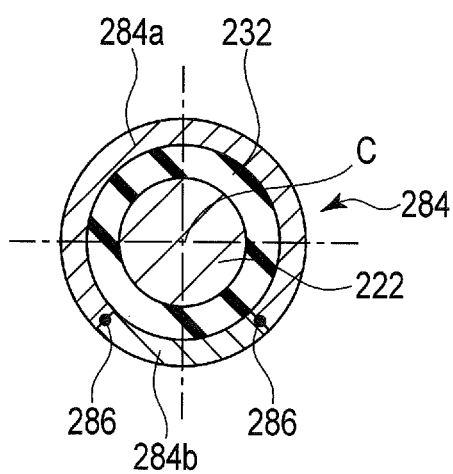
FIG. 15B is a schematic transverse cross-sectional view taken along a line of arrows 15B-15B in FIG. 15A, showing the treatment device according to the fifth reference case.

A fifth reference case will now be described with reference to FIG. 15A and FIG. 15B. This reference case is a modification of the first to fourth reference cases. In particular, this reference case is a modification of the second reference case.

Like the sheath 254 of the treatment device 210 according to the second reference case, a sheath 284 of a treatment device 210 according to the fifth reference case is formed by welding two split members. The sheath 284 has a C-shaped pipe 284a having a substantially C-like transverse cross section and an arc-shaped pipe 284b having a substantially arc-like transverse cross section. One circle is formed by fitting the C-shaped pipe 284a and the arc-shaped pipe 284b to each other.

In the C-shaped pipe 284a, a portion having a C-like transverse cross section and a portion having a semicircular transverse cross section are alternately formed in an axial direction of a central axis C. In the arc-shaped pipe 284b, an arc portion whose transverse cross section is shorter than a semicircle and an arc portion having a semi-circular transverse cross section are alternately formed in the axial direction of the central axis C. Therefore, the C-shaped pipe 284a and the arc-shaped pipe 284b can be fitted to each other.

The divided end faces of the C-shaped pipe 284a and the arc-shaped pipe 284b are arranged to contact on each other, and these pipes are fixed in this state by, e.g., laser welding. That is, end portions of the C-shaped pipe 284a and the arc-shaped pipe 284b are fixed at welding portions 286. In this reference case, an O-ring 232 is supported by the C-shaped pipe 284b. Therefore, a holding force of the probe main body section 222 at a position of the O-ring 232 is improved as compared with the second reference case. That is, in this reference case, a longitudinal axis L of the probe 212 can be easily matched with the central axis C of the sheath 284 as compared with a relationship between the probe 212 and the sheath 254 in the second reference case.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment assembly comprising:
   a probe that includes a treatment section at a distal end portion of the probe, the probe being configured to transmit an ultrasonic vibration from a proximal end portion of the probe to the distal end portion of the probe;
   an elastic annular member disposed on the probe at a node position of the ultrasonic vibration;
   an inner tube that includes a distal end and a proximal end, and into which the treatment section of the probe is able to be inserted through the proximal end of the inner tube to the distal end of the inner tube such that the treatment section of the probe protrudes toward a distal end side with respect to the distal end of the inner tube;
   an opening that is provided in a side surface of the inner tube, the opening allowing an inner side of the inner tube to communicate with an outer side of the inner tube, the opening being located at the node position of the ultrasonic vibration;
   a support section that is arranged on the inner side of the inner tube from the outer side of the inner tube through the opening, the support section being configured to contact the elastic annular body so as to support the probe with respect to the inner tube; and
   an outer tube that radially covers the outer side of the inner tube and that radially covers the support section, the outer tube fixing the support section in the opening.

2. The treatment assembly according to claim 1, wherein:
   a longitudinal axis is defined in the probe;
   a central axis is defined in the inner tube; and
   the outer tube is configured to fix the support section in a state that the longitudinal axis of the probe is matched with the central axis of the inner tube.

3. The treatment assembly according to claim 2, wherein the distal end portion of the probe is asymmetrical with respect to the longitudinal axis, and includes: (i) a distal tip that is disposed away from the longitudinal axis, and (ii) a proximal tip that is disposed close to the longitudinal axis with respect to the distal tip.

4. The treatment assembly according to claim 3, wherein a length obtained by combining a distance from the longitudinal axis to the distal tip with a distance from the longitudinal axis to the proximal tip is smaller than a minimum inner diameter of the inner tube.

5. The treatment assembly according to claim 3, wherein:
   the inner tube includes a slit that extends at least from the distal end toward a proximal end side of the inner tube, the distal tip of the distal end portion of the probe is passed through the slit, and
   a length obtained by combining a distance from the longitudinal axis to the distal tip with a distance from the longitudinal axis to the proximal tip is larger than a minimum inner diameter of the inner tube.

6. The treatment assembly according to claim 1, wherein:
   the opening of the inner tube is formed at a position corresponding to the node position of the ultrasonic vibration, which is a first node position from the distal end of the inner tube toward a proximal end side in a state that the probe is supported by the support section with respect to the inner tube.

7. The treatment assembly according to claim 6, wherein, in addition to the opening, the inner tube includes a different opening that allows the inner side of the inner tube to communicate with the outer side of the inner tube, the different opening of the inner tube being in the side surface of the inner tube on a distal end side apart from the proximal end on the proximal end side of the opening.

8. The treatment assembly according to claim 7, wherein:
   a central axis is defined in the inner tube, and
   the different opening is arranged at a position deviated from the central axis of the inner tube in the circumferential direction with respect to the opening.

9. The treatment assembly according to claim 1, wherein:
   a central axis is defined in the inner tube,
   the opening includes: (a) a pair of first edge portions formed to be parallel to an axial direction of the central axis of the inner tube, and (b) a pair of second edge portions which are orthogonal to the axial direction of the central axis of the inner tube and have opposed arc-shaped surfaces, and
   the support section includes: (i) an arc-shaped portion, and (ii) a pair of leg portions integrally formed with the arc-shaped portion.

10. The treatment assembly according to claim 1, wherein:
    the elastic annular body is provided at the node position of the ultrasonic vibration that is closest to the distal end portion of the probe, the elastic annular body including: (i) an annular portion, and (ii) an arc-shaped concave portion formed by removing part of the outer side of the annular portion into an arc-like shape, and
    the support section has an arc-shaped body arranged in the arc-shaped concave portion of the annular body through the opening.

11. The treatment assembly according to claim 10, wherein the arc-shaped body includes: (i) one end, (ii) another end and (iii) engagement sections engaging with the opening at the one end and the another end, respectively.

12. The treatment assembly according to claim 1, further comprising an O-ring disposed between an inner peripheral surface of the inner tube and an outer peripheral surface of the probe.

13. A treatment device comprising:
    the treatment assembly according to claim 1; and
    a handle that is configured to support a proximal end portion of the probe and a proximal end of the inner tube.

14. The treatment device according to claim 13, wherein, in addition to the opening, the inner tube includes a different opening, which allows the inner side of the inner tube to communicate with the outer side of the inner tube, the different opening being disposed: (i) in the side surface of the inner tube on a distal end side apart from the proximal end, and (ii) on a distal end side of a distal end of the handle on a proximal end side of the opening.

15. The treatment device according to claim 14, wherein the different opening of the inner tube is placed at a position corresponding to another node position of the ultrasonic vibration which is a first node position from the distal end of the handle on the distal end side.

16. A manufacturing method of the treatment assembly according to claim 1, the method comprising:
    protruding the distal end portion of the probe towards a distal end side with respect to the distal end of the inner tube after protruding through the proximal end of the inner tube to the distal end of the inner tube;
    arranging the support section in the opening of the inner tube and supporting the probe by the support section; and
    covering an outer side of the inner tube with the outer tube to fix the support section to the inner tube and the outer tube.

17. The treatment assembly according to claim 1, wherein the support section has an arc-shape.

* * * * *